US009078983B2

(12) United States Patent
Herr

(10) Patent No.: US 9,078,983 B2
(45) Date of Patent: Jul. 14, 2015

(54) PREFILLED SAFETY PEN NEEDLE

(71) Applicant: Becton, Dickinson and Company, Franklin Lakes, NJ (US)

(72) Inventor: Joshua Herr, Fair Lawn, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/970,125

(22) Filed: Aug. 19, 2013

(65) Prior Publication Data

US 2015/0051578 A1  Feb. 19, 2015

(51) Int. Cl.
*A61M 5/50* (2006.01)
*A61M 5/32* (2006.01)
*A61M 5/24* (2006.01)
*A61M 5/28* (2006.01)
*A61M 5/315* (2006.01)
*A61M 5/20* (2006.01)

(52) U.S. Cl.
CPC . *A61M 5/50* (2013.01); *A61M 5/24* (2013.01); *A61M 5/288* (2013.01); *A61M 5/3158* (2013.01); *A61M 5/31585* (2013.01); *A61M 5/31591* (2013.01); *A61M 5/321* (2013.01); *A61M 5/3202* (2013.01); *A61M 5/326* (2013.01); *A61M 5/3213* (2013.01); *A61M 5/3243* (2013.01); *A61M 5/3271* (2013.01); *A61M 5/3272* (2013.01); *A61M 5/2033* (2013.01); *A61M 2005/206* (2013.01); *A61M 2005/2407* (2013.01); *A61M 2005/3247* (2013.01); *A61M 2005/3263* (2013.01); *A61M 2005/3267* (2013.01); *A61M 2205/273* (2013.01)

(58) Field of Classification Search
CPC ..... A61M 5/24; A61M 5/3271; A61M 5/326; A61M 2005/3254; A61M 25/0631
USPC ......... 604/201, 187, 192, 194, 197, 198, 244, 604/506, 207, 246
See application file for complete search history.

(56) References Cited

U.S. PATENT DOCUMENTS

| | | | | |
|---|---|---|---|---|
| 3,605,744 A | * | 9/1971 | Dwyer | 604/506 |
| 5,279,586 A | * | 1/1994 | Balkwill | 604/207 |
| 5,542,760 A | | 8/1996 | Chanoch et al. | |
| 5,961,495 A | | 10/1999 | Walters et al. | |
| 6,096,010 A | * | 8/2000 | Walters et al. | 604/207 |
| 6,221,053 B1 | | 4/2001 | Walters et al. | |
| 6,248,095 B1 | | 6/2001 | Giambattista et al. | |
| 6,277,099 B1 | | 8/2001 | Strowe et al. | |
| 6,585,698 B1 | | 7/2003 | Packman et al. | |
| 6,932,794 B2 | | 8/2005 | Giambattista et al. | |
| 6,936,032 B1 | | 8/2005 | Bush, Jr. et al. | |
| 7,018,364 B2 | | 3/2006 | Giambattista et al. | |
| 7,645,264 B2 | | 1/2010 | Marsh et al. | |

(Continued)

FOREIGN PATENT DOCUMENTS

WO   WO-03045480 A1   6/2003
WO   WO-2005035030 A1   4/2005

(Continued)

*Primary Examiner* — Nicholas Lucchesi
*Assistant Examiner* — Anh Bui
(74) *Attorney, Agent, or Firm* — Roylance, Abrams, Berdo & Goodman, L.L.P.

(57) ABSTRACT

A pre-filled, single-use injection device includes a passive dual shield on the patient end of the needle. The device is self-contained so that the entire needle is shielded after use without a separate passive shield system for the non-patient end.

20 Claims, 2 Drawing Sheets

(56) References Cited

U.S. PATENT DOCUMENTS

| | | |
|---|---|---|
| 7,850,663 B2 | 12/2010 | Sullivan et al. |
| 2004/0225262 A1* | 11/2004 | Fathallah et al. ............ 604/198 |
| 2005/0187523 A1* | 8/2005 | Giambattista et al. ........ 604/207 |
| 2010/0286605 A1 | 11/2010 | Klug et al. |
| 2011/0257603 A1* | 10/2011 | Ruan et al. .................... 604/198 |
| 2011/0288491 A1 | 11/2011 | Newman et al. |
| 2012/0123346 A1* | 5/2012 | Davies et al. ................. 604/191 |
| 2012/0172793 A1 | 7/2012 | Cronenberg et al. |

FOREIGN PATENT DOCUMENTS

| | | |
|---|---|---|
| WO | WO-2009114762 A1 | 9/2009 |
| WO | WO-2009114777 A1 | 9/2009 |

* cited by examiner

PREFILLED SAFETY PEN NEEDLE

BACKGROUND OF THE INVENTION

1. Field of the Invention

The invention is in the field of injection devices for delivering medications, and specifically to a pre-filled single-use device which protects the user or health care provider from accidental needle-stick.

2. Description of the Related Art

The prior art teaches various safety shield systems adapted for use with a medication pen. Examples of passive shielding systems include those disclosed in U.S. Patent Application Publication Nos. 2011/0288491 and 2011/0257603, which are incorporated by reference. The needle assemblies disclosed in these publications are adapted to attach to a pen body, and include a proximal or non-patient side needle which extends into the medication compartment of the pen. In addition to shielding the patient-side needle, such shield systems may include a manually or passively activated shield for covering the proximal side needle to prevent accidental needle stick when the shield assembly is removed from the pen body.

With the growth of filled pen devices and other formulations approved for self-injection, the demand for single-use injection devices is likely to increase. It is an object of the present invention to apply the teaching of passive shield protection to a disposable, single use injection device having a self-contained construction such that the patient end of the needle is passively shielded before and after use and the non-patient end of the needle is contained within the device to protect the user or health care provider from needle sticks without requiring a passive shield system on the non-patient end.

SUMMARY OF THE INVENTION

In one aspect, the invention is an injection device comprising a hub bearing a needle. The hub has a proximal slot for engaging a thumb button and a distal surface for engaging a shield assembly. The shield assembly comprises an inner shield radially outward of the needle which has features engaging the hub. The shield assembly further comprises an outer shield radially outward of the inner shield which is adapted to retain the inner shield in an initial position and to release the inner shield to a second position covering the needle. The shield assembly also comprises an outer sleeve radially outward of the outer shield. A first spring biases the inner shield in a distal direction covering the needle after use. A small-volume reservoir containing medication is provided in the device adapted to be pierced by the proximal end of the needle cannula to provide fluid connection between the reservoir and the needle cannula. A thumb button having a tab engages the proximal slot on the hub and encloses the reservoir between the thumb button and the hub. The thumb button has a plunger on a proximal side thereof engaging the reservoir to dispense medication from the distal end of the needle.

In another aspect, the invention is a method of using the device to administer a single dose of medication by injection and passively contain the distal and proximal ends of the needle after use. The method comprises: providing a single use injection device having a hub bearing a needle, the hub having a proximal slot for engaging a thumb button and a distal surface for engaging a passive shield assembly; a small-volume reservoir containing medication adapted to be pierced by the proximal end of the needle to provide fluid connection between the reservoir and the needle cannula; and a thumb button having a tab engaging the proximal slot on the hub and enclosing the reservoir between the thumb button and the hub, the thumb button having a plunger on a proximal side thereof engaging the reservoir to dispense medication from the distal end of the needle. To administer the injection, the patient or health care professional positions the single use device against the injection site and depresses the thumb button to deliver the single dose by injection. The distal end of the needle is passively shielded after use using any means, including the dual shield embodiment described above using an inner and outer shield arranged around the distal end of the hub and needle. Thus, both ends of the needle cannula are protected, the distal end is passively shielded to prevent accidental needle stick from the distal end of the needle before and after injection and the proximal end of the needle is contained between the thumb button and the hub after use to protect the user against accidental needle stick from the proximal end of the needle. As an additional benefit, the single use device prevents cross-contamination which could be caused by re-use of a pen with a different pen needle.

As will be evident to the person of ordinary skill in the art from the following detailed description, variations of the above-described single use device and method of using same may be adapted and practiced without departing from the scope of the invention.

DETAILED DESCRIPTION OF THE INVENTION

As used herein, the "distal" direction is in the direction of the injection site, and the "proximal direction" is the opposite direction. The "axial" direction is along the longitudinal axis of the injection device. The needle cannula is generally arranged axially in the device. "Radially" is a direction perpendicular to the axial direction. Thus, "radially inward" generally means closer to the needle. "Integral" means one-piece in the state normally encountered by the user—not intended to be taken apart easily.

Figure 1:
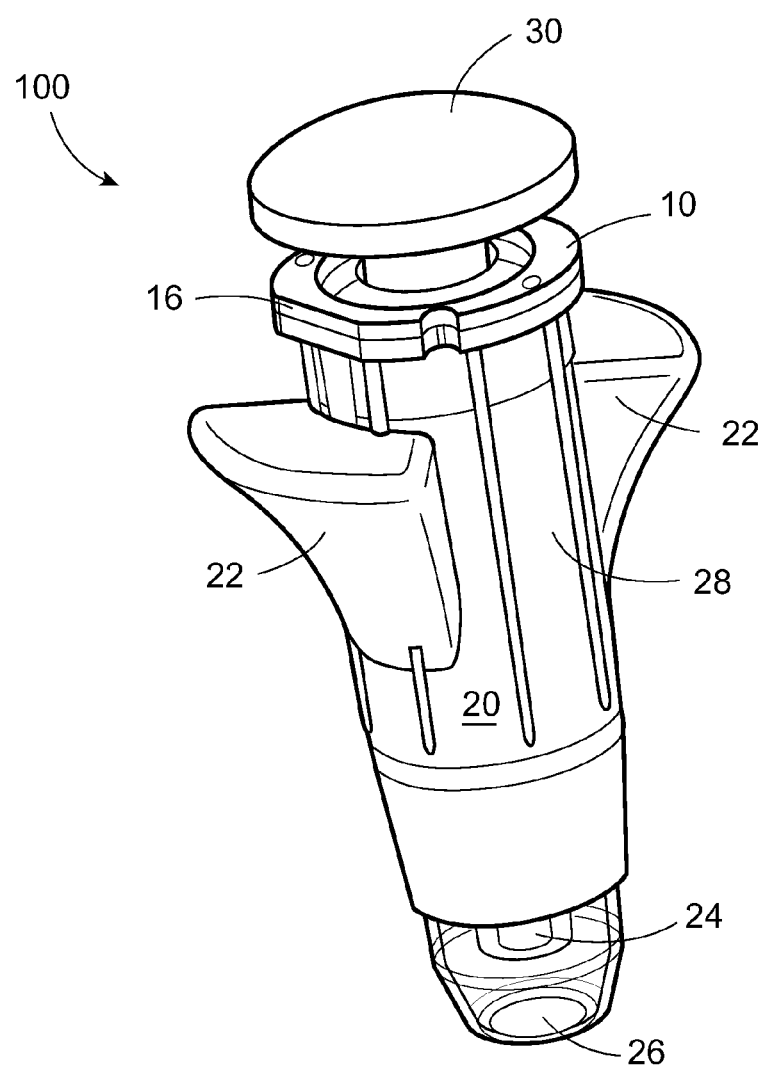
FIG. 1 depicts a perspective view of the single-use injection device of the invention.

A single use device 100 according to an embodiment of the invention is shown in FIG. 1 in the state encountered by a user. Needle-bearing hub 10 is completely contained within a shield assembly 20 such that the outer sleeve 28 of the shield assembly 20 itself becomes the body of the device. Only a lip 16 of the hub 10 sits outside the shield assembly, for attachment using an interference fit, heat welding, adhesive, a combination thereof, or other technique known in the art. Similar to existing shield systems, such as the Autoshield DUO™, the shield assembly 20 may comprise an outer shield 26 which covers the needle in an initial state, and an inner shield 24 from which the needle protrudes in the initial state. (Needle 56 is not shown in FIG. 1.) The outer shield 26 retains the inner shield 24 in the initial state and moves proximally to release an inner shield 24 from the initial state. A variety of releasable retaining means may be employed to retain and release the inner shield 24, as described below. Once released, the inner shield 24 is biased by a spring to a second position covering the needle. The inner shield is preferably locked out over the needle in the second, after-use position. Both shields are at least partially encircled by outer sleeve 28. Wings 22 may be formed on the outer surface of the outer sleeve 28 to provide a finger-hold for the user or health care provider delivering an injection. Generally the inner shield 24, outer shield 26 and sleeve 28 are made of injection molded plastic, such as polypropylene. Materials and methods of manufacture may be adapted from the medication pen prior art.

Figure 2:
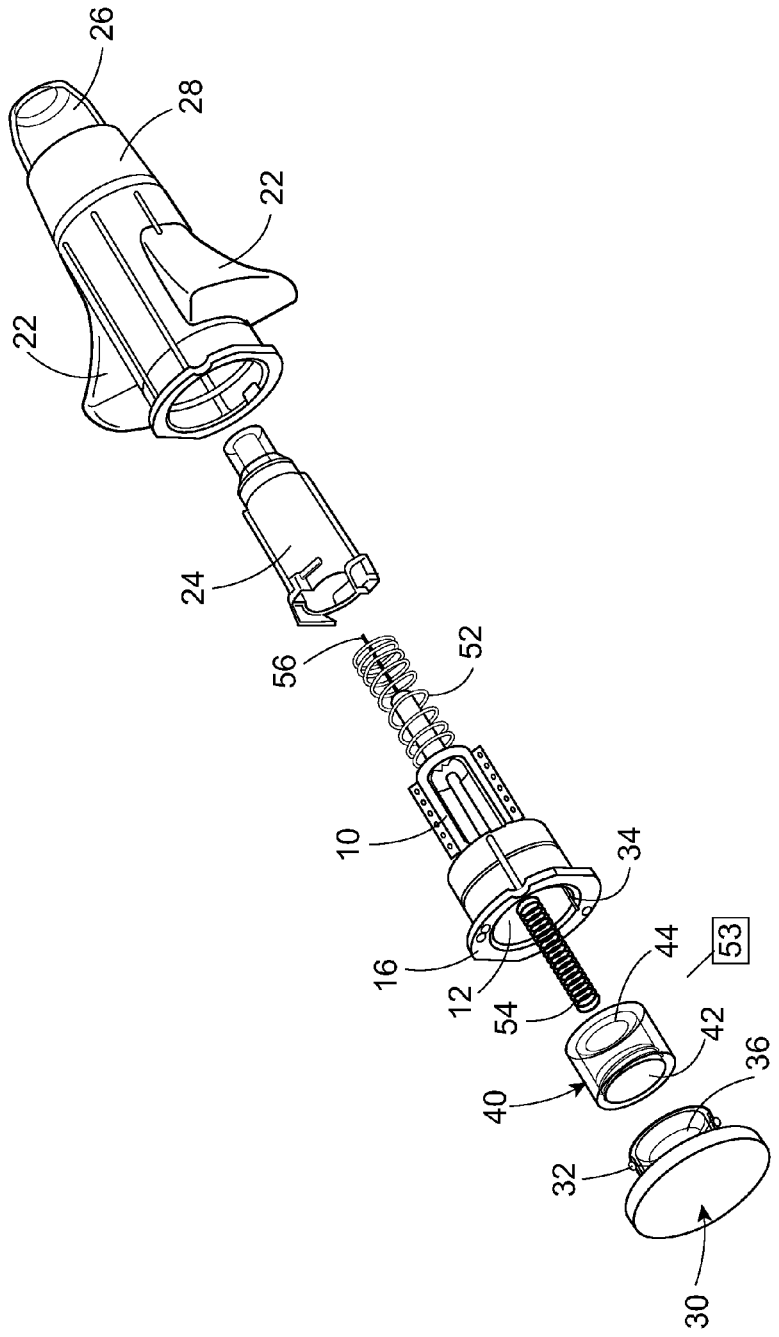
FIG. 2 is an exploded view of the device of FIG. 1.

A more detailed view of the assembly is seen in the exploded view of FIG. 2. Rather than adapting the hub 10 for attachment to a pen body, as in the prior art, the hub 10 according to the present invention is adapted for single-use operation by providing a proximal opening 12 on the hub 10 to receive thumb button 30 and a pre-filled, small-volume reservoir 40 containing medication between the thumb button 30 and the hub 10. According to the preferred embodiments, the opening 12 in the hub is adapted to receive substantially the entirety of the reservoir.

The thumb button is guided by tabs 32 that interface with slots 34 on an interior surface of the hub. In embodiments, tabs 32 and axially oriented slots 34 cooperate to cause the thumb button 30 to travel axially, without rotation, when the thumb button is depressed during an injection. In further embodiments, slots 34 on the interior surface of the hub are circumferentially oriented so that the thumb button can be rotated within the proximal opening 12 of the hub. Of course, both axial and circumferential grooves may be provided on the hub to guide the movement of the thumb button in the hub. For example, in one embodiment, the thumb button 30 is prevented from axial movement in a first position, and must be rotated to a position in which tabs 32 engage axially oriented slots for axial movement. Thus, the thumb button may be rotated from a safety position in which injection is not enabled to a position in which injection is enabled. Although the thumb button 30 may move within the hub 10, the thumb button is not removable by the user during normal use. An advantage of the single-use device is its overall compactness—in embodiments, the length of the device from the proximal end of the thumb button to the distal end of the outer shield may be less than 60 mm, accommodating a standard 4 mm, 5 mm or 8 mm injection depth needle. The single use shielded device may also be used with longer or shorter needles, including intradermal injection depth needles.

The interface of the thumb button 30 directly with the hub 10 permits user-friendly adaptation of the single-use injection device. For example, prefilled reservoir 40 may be engaged to the thumb button 30 so that the reservoir 40 rotates with the thumb button within opening 12 in the hub. Slots 34 in the hub may be configured so that rotating the thumb button 30 in the hub 10 allows the reservoir 40 to be moved from a first axial position, in which the proximal end of the needle cannula cannot pierce the septum 44 of the reservoir, to an injection-ready position, in which the septum can be pierced by the thumb button.

In another embodiment, the interface of the thumb button 30 and the hub 10 allows the user or health care provider to select from a plurality of dose levels. In this embodiment, a plurality of axially oriented slots provide for longer or shorter axial movement of the thumb button within the hub 10. Depending on the axial position of the thumb button, plunger 36 on the thumb button 30 engages stopper 42 on the reservoir to a different axial position, ejecting a corresponding dose of medication from the needle 56.

In another embodiment, the thumb button is provided with a locked after-use position. For this purpose, tabs on the thumb button may be provided to mate with corresponding features on the hub in a locking relationship. These corresponding features are adapted to lock at or close to the distal-most position of the thumb button, reached after an injection is administered. In the locked after-use position, the thumb button cannot be removed, and proximal, distal and/or rotational movement of the thumb button is prevented. The exact arrangement, size and number of the corresponding features on the hub and the thumb button for this purpose may be left to the judgment of the person of ordinary skill. Instead of tabs on the thumb button engaging recesses on the hub, tabs on the hub could be made to mate with recesses on the thumb button. Engagement of the corresponding features in a locked after-use position may be accompanied by an audible click to indicate that an injection is complete.

The thumb button may comprise a plurality of components. In embodiments, a threaded interface may be provided between the thumb button and the hub so that a component of the thumb button rotates as it is pushed down, similar to some existing medication pens. Typically the rotating component of the thumb button is a separate molded plastic piece located underneath the exterior surface contacted by the user.

Single-use reservoir 40 is simpler than a medication pen cartridge because it is adapted to be shipped to the user pre-filled. Thus, the user is not required to install a pen needle on a pen body. However, similar to a medication pen cartridge, the reservoir typically comprises a septum 44, which is pierced by proximal end of needle 56 during an injection. Stopper 42 seals off the reservoir and can be pushed to pressurize the contents of the reservoir to eject medication from the distal end of needle 56. However, any medication holder capable of being pierced by the needle and compressed to eject medication may be used in place of the above-described cartridge with septum and stopper without departing from the scope of the invention, including for example a flexible plastic ballast. Usable with any medication that is delivered subcutaneously, the single-use system is advantageously adapted for use with fixed-dose medications, including, without limitation, epinephrine (and other hormone therapies), basal insulin, glucagon-like peptide (GLP-1), leukocyte growth factors, osteoporosis medications such as Forteo®, hormone-based diabetic therapies such as Pramlintide®, and the like.

Different mechanisms may be employed to prevent septum 44 from being pierced by the needle 56 prior to injection. In one embodiment, spring 54 is utilized between the needle bearing hub 10 and the pre-filled reservoir 40. Upon depressing the thumb button 30, spring 54 compresses and the proximal end of the needle 56 punctures the reservoir septum 44 to create an open fluid path for the medication. Further depressing the button delivers medication to the patient.

Other means of preventing the proximal end of needle 56 from piercing the reservoir septum may be adapted for use with the pre-filled device of the invention. For example, a breakable plastic retainer 53 may be used to retain the reservoir in a safety position which is broken by engaging the thumb button 30. Alternatively, as described above, the reservoir is engaged with the thumb button and is moved axially into a position where the septum can be pierced simply by rotating the thumb button 30.

The disposable device obviates the need for a proximal end shield because the proximal end of the needle is contained within the device when disposed of. The distal end shield system may be adapted from prior art shield systems, including the above-referenced U.S. Patent Application Publication No. 2011/0257603, with few modifications.

As an example, according to one preferred embodiment of the invention, the outer shield 26 is pushed into sleeve 28 during an injection, triggering the release of inner shield 24, and upon withdrawal of the device from the patient's tissue, the inner shield 24 fully extends through the opening on the distal end of the outer shield into a locked position under bias of the spring 52. In the after-use position, the inner shield 29 extends beyond the cannula tip, guarding the contaminated tip against accidental needlestick and providing an indication that the device has been used.

Automatically releasing the inner shield by proximally moving the outer shield may be accomplished in a variety of ways. To achieve shielding operation according to one preferred embodiment of the invention, outer shield 26 engages grooves on an internal surface of the outer sleeve 28 to prevent rotation of the outer shield relative to the shield assembly during initial proximal movement of the outer shield 26. Meanwhile, protrusions on the hub nest within lobes formed on the inner shield, to prevent rotation of the inner shield 29 relative to the shield assembly. Further, the inner and outer shields 26, 24 are configured with tapered surfaces, arranged so that when the outer shield 26 is telescoped over the inner shield 24 in the initial position, the tapered surfaces abut one another. Proximal movement of the outer shield 26 into the outer sleeve 28, after the outer shield clears the grooves on the outer sleeve, causes the tapered surfaces to slide against each other to rotate the outer shield 26. This rotation of the outer shield frees the inner shield to move distally under the bias of spring 52 to a position in which the inner shield 24 covers the needle. The inner shield may engage recesses in the outer sleeve or hub to lock out the inner shield in this after-use state.

In this preferred embodiment, outer shield 26 has a distal opening through which the distal end of the inner shield 24 passes when it is biased to the after-use position covering the needle. The outer shield 26 has a tapered shape on the distal end, and a corresponding shoulder portion of the inner shield 24 fits within this tapered portion of the outer shield in the after-use position.

Administering an injection with the single-use device according to the invention is substantially the same as administering an injection with a medication pen according to the prior art. The single use device, being smaller, may be more easily manipulated with one hand because of the proximity of the thumb button to the finger holds on the outer sleeve. However, preparing the device for an injection is considerably simplified, because the user is not required to attach a pen needle to a pen body prior to performing the injection or to remove the pen needle after an injection. In the case of a fixed dose embodiment, the user is not required to set the dose.

The above described embodiments provide many advantages compared to current medication injection devices and practices using syringes or medication pens and pen needles. Because the needle assembly according to the invention is self-contained, the device provides added convenience compared to the current practices requiring either vial and syringe, or a medication pen and separate pen needle. Further, this concept offers a solution to the risk of cross-contamination between patients in institutional settings compared to pens or syringes because the single-use device locks the cannula from re-use after removal from the patient and provides an indication that the device has been used. Because the device is so much smaller than typical syringes or medication pens and pen needles, it can be disposed of easily after a single use. The above-described embodiments should not be construed as limiting the invention, which is defined in the appended claims.

The invention claimed is:

1. A single-use injection device, comprising:
 a hub bearing a needle, having a proximal slot for engaging a thumb button and a distal surface for engaging a shield assembly;
 the shield assembly comprising an inner shield radially outward of the needle and having features engaging the hub, an outer shield radially outward of the inner shield adapted to cover the needle in an initial state and retain the inner shield in an initial position and to move proximally to release the inner shield from said initial position to a second position covering the needle after an injection, and an outer sleeve radially outward of the outer shield;
 a first spring biasing the inner shield in a distal direction covering the needle;
 a small-volume reservoir containing medication, adapted to be pierced by the needle to provide fluid communication with the needle cannula; and
 an axially displaceable thumb button having a tab engaging the proximal slot on the hub and enclosing the reservoir between the thumb button and the hub, the thumb button having a plunger engaging the reservoir to dispense medication from the distal end of the needle.

2. The injection device according to claim 1, wherein the reservoir is a cartridge having a stopper on one side adapted to be compressed by the thumb button and a septum on a side opposite said one side adapted to be pierced by the needle.

3. The injection device according to claim 1, further comprising means to prevent the needle from puncturing the reservoir septum prior to use.

4. The injection device according to claim 1, wherein the medication is a single dose approved for self-injection.

5. The injection device according to claim 1, wherein the medication is a single dose of basal insulin, glucagon-like peptide (GLP-1), leukocyte growth factor, an osteoporosis medication, or hormone-based diabetic therapy.

6. The injection device according to claim 1, wherein the outer sleeve includes wings extending from the outer surface of the outer sleeve, shaped to provide a finger hold to facilitate handling.

7. The injection device according to claim 1, wherein the thumb button is rotatable to set a dosage level.

8. The injection device according to claim 1, wherein the thumb button is integrally attached to the hub.

9. The injection device according to claim 1, further comprising corresponding features on the hub and thumb button which mate when the thumb button is at or close to a distal-most position of the thumb button with respect to the hub, wherein the mating of the corresponding features on the hub and the thumb button prevents proximal, distal and/or rotational movement of the thumb button.

10. The injection device according to claim 1, comprising a second spring positioned between the hub and the pre-filled reservoir biasing the needle in a direction away from the reservoir and preventing the needle from puncturing the reservoir septum prior to use.

11. The injection device according to claim 1, wherein the thumb button is rotatable from a safety position to an injection position, in which an injection may be administered by pressing the thumb button.

12. The injection device according to claim 1, wherein the reservoir is rotatable from a position preventing the needle from puncturing the reservoir septum prior to use to an injection position, in which an injection may be administered by pressing the thumb button.

13. The injection device according to claim 1, wherein a breakable member prevents the reservoir septum from being pierced by the needle prior to use.

14. The injection device according to claim 1, wherein the outer shield rotates from the initial position in which the inner shield is retained, to the second position in which the inner shield is freed to move distally to cover the needle under bias of the first spring.

15. The injection device according to claim 1, wherein the length of the device from the proximal end of the thumb button to the distal end of the outer shield is 60 mm or less, accommodating a standard 4 mm, 5 mm, or 8 mm injection depth needle.

16. A method of injecting a single dose of medication and passively containing the distal and proximal ends of a needle used for the injection after use, comprising:

providing a single use injection device having a hub bearing a needle, the hub having a proximal slot for engaging a thumb button and a distal surface for engaging a passive shield assembly;

a small-volume reservoir containing medication adapted to be pierced by the needle to provide fluid communication with the needle cannula; and a thumb button having a tab engaging the proximal slot on the hub and enclosing the reservoir between the thumb button and the hub, the thumb button having a plunger on a proximal side thereof engaging the reservoir to dispense medication from the distal end of the needle;

said passive shield assembly comprising an inner shield radially outward of the needle and having features engaging the hub and an outer shield radially outward of the inner shield adapted to cover the needle in an initial state and engage the inner shield to retain the inner shield in an initial position;

positioning the single use device against the injection site;

moving the outer shield proximally into the outer sleeve to release the inner shield from the initial position; and depressing and axially displacing the thumb button to deliver the single dose by injection;

passively shielding the distal end of the needle after use while the proximal end of the needle is contained between the thumb button and the hub; and disposing of the single use injection device.

17. The method according to claim 16, further comprising rotating the thumb button prior to use to an injection position in which an injection may be administered by pressing the thumb button.

18. The method according to claim 16, further comprising locking the thumb button in a distal position after use with mating features on the hub and the thumb button wherein proximal, distal and/or rotational movement of the thumb button is prevented in the after use position.

19. The method according to claim 16, further comprising rotating the thumb button to select a dosage.

20. The method according to claim 16, wherein the single dose of medication is basal insulin, glucagon-like peptide (GLP-1), leukocyte growth factor, an osteoporosis medication or hormone-based diabetic therapy, approved for self-administration.

* * * * *